(12) United States Patent
Hulliger et al.

(10) Patent No.: US 8,500,784 B2
(45) Date of Patent: Aug. 6, 2013

(54) VARIABLE ANGLE SCREW PLATE SYSTEMS

(75) Inventors: Urs Hulliger, Deitingen (CH); Robert Frigg, Bettlach (CH)

(73) Assignee: Depuy Synthes Products, LLC, Raymham, MA (US)

( * ) Notice: Subject to any disclaimer, the term of this patent is extended or adjusted under 35 U.S.C. 154(b) by 317 days.

(21) Appl. No.: 12/763,696

(22) Filed: Apr. 20, 2010

(65) Prior Publication Data
US 2011/0098754 A1    Apr. 28, 2011

Related U.S. Application Data

(60) Provisional application No. 61/181,149, filed on May 26, 2009.

(51) Int. Cl.
*A61B 17/86* (2006.01)
*A61B 17/80* (2006.01)

(52) U.S. Cl.
USPC ........................................................ 606/305

(58) Field of Classification Search
USPC ................ 606/60, 70, 71, 246–299, 300, 331
See application file for complete search history.

(56) References Cited

U.S. PATENT DOCUMENTS

| | | | | |
|---|---|---|---|---|
| 5,902,303 | A * | 5/1999 | Eckhof et al. | 606/60 |
| 6,235,033 | B1 * | 5/2001 | Brace et al. | 606/288 |
| 7,048,739 | B2 * | 5/2006 | Konieczynski et al. | 606/288 |
| 7,063,701 | B2 * | 6/2006 | Michelson | 606/307 |
| 7,988,714 | B2 * | 8/2011 | Puekert et al. | 606/291 |
| 8,100,955 | B2 * | 1/2012 | Blain et al. | 606/291 |
| 8,114,141 | B2 * | 2/2012 | Appenzeller et al. | 606/328 |
| 2006/0122604 | A1 * | 6/2006 | Gorhan et al. | 606/69 |
| 2006/0264936 | A1 * | 11/2006 | Partin et al. | 606/61 |
| 2008/0288000 | A1 * | 11/2008 | Cawley | 606/291 |

FOREIGN PATENT DOCUMENTS

| | | |
|---|---|---|
| WO | 00/66045 | 11/2000 |
| WO | 01/03592 | 1/2001 |
| WO | 2008/115318 | 9/2008 |

* cited by examiner

*Primary Examiner* — Kevin T Truong
*Assistant Examiner* — Christopher Beccia
(74) *Attorney, Agent, or Firm* — Fap Kaplun & Marcin, LLP

(57) ABSTRACT

A bone fixation element comprises a shaft extending longitudinally from a proximal end to a distal end and a head connected to the proximal end of the shaft. The head includes a radially outer abutting structure deformable to lockingly engage an inner wall of an opening through a bone plate. Deformation of the abutting structure permits the head to lock the bone fixation element within the opening at any user-selected angle with respect to a central axis of the opening within a permitted range of angulation.

6 Claims, 13 Drawing Sheets

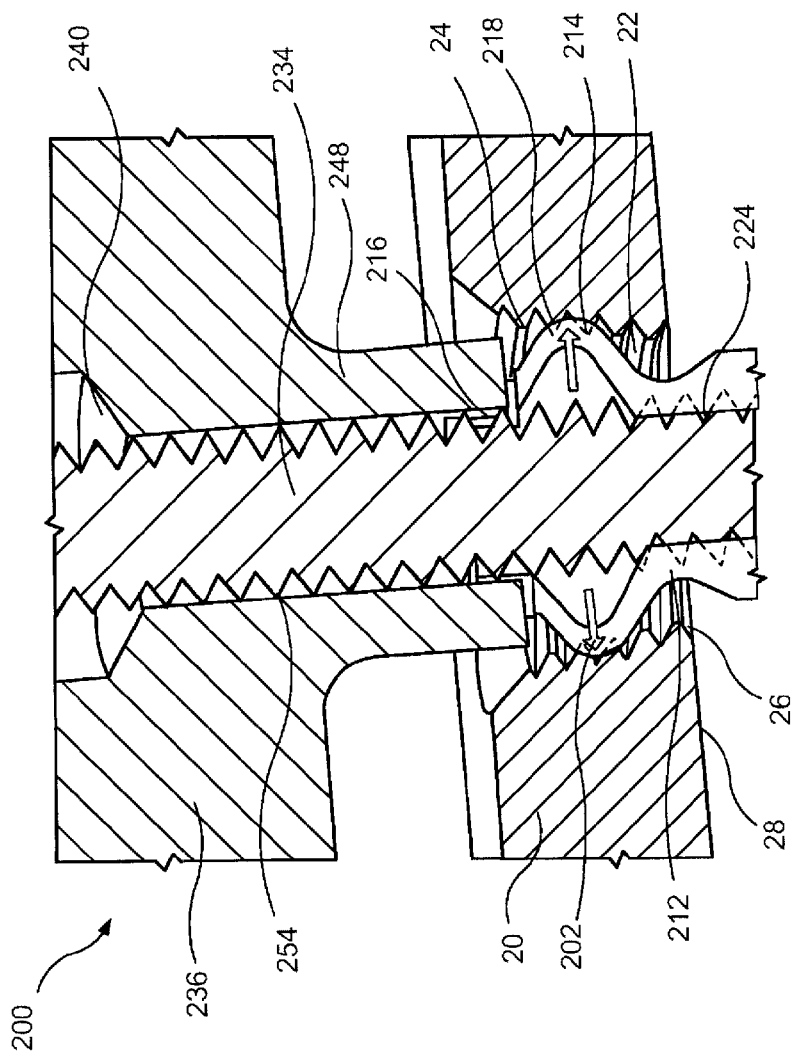

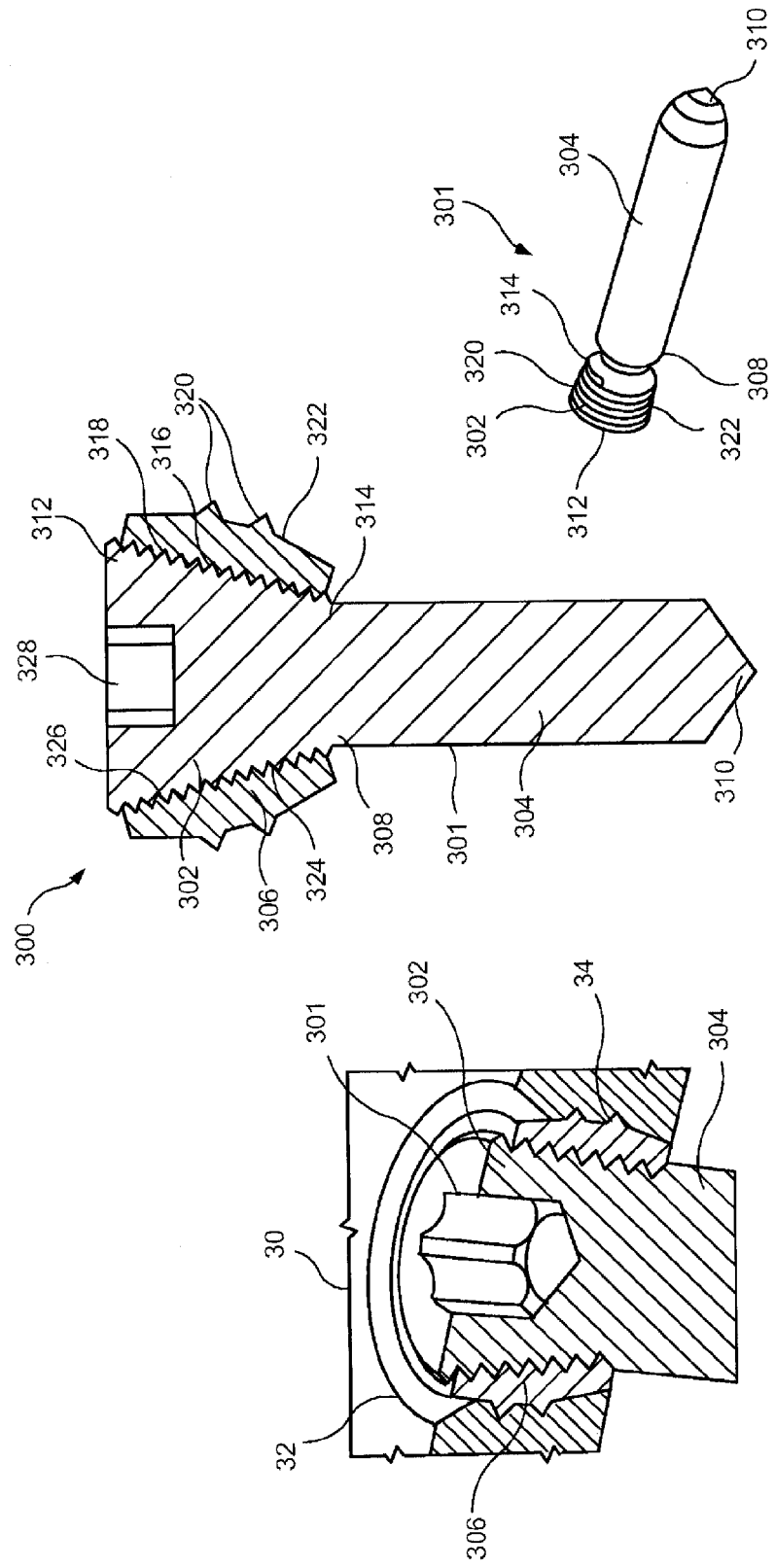

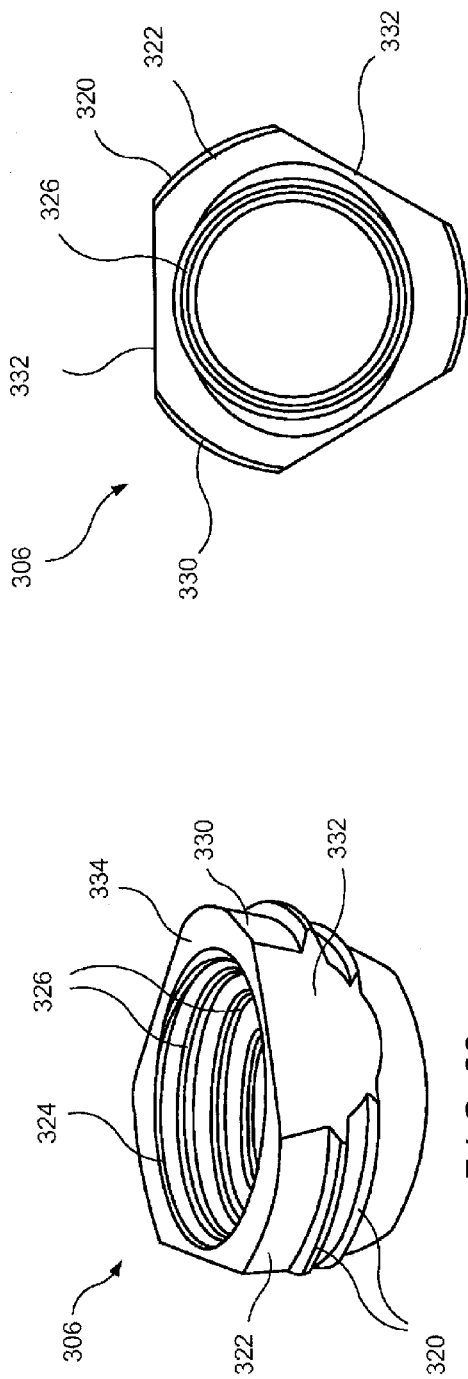
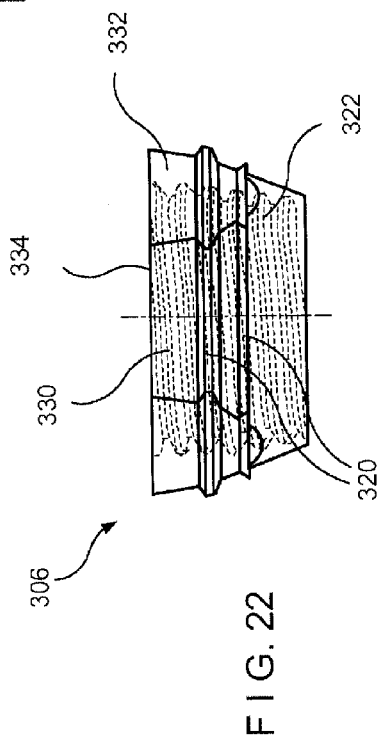

VARIABLE ANGLE SCREW PLATE SYSTEMS

PRIORITY CLAIM

The present application claims priority to U.S. Provisional Application Ser. No. 61/181,149 filed on May 26, 2009 entitled "Variable Angle Screw Plate Systems," the entire disclosure of which is incorporated herein by reference

FIELD OF THE INVENTION

The present invention relates to devices for treating fractures and, in particular, relates to devices for fixing implants, such as bone plates, to bone.

BACKGROUND

In certain orthopedic surgical procedures, it is often necessary to secure multiple bones or bone portions relative to one another. Various plating systems for internal fixation of a variety of bones are known. Such systems generally include a plate attached to the bone or bone portions spanning a fracture line or a spinal disk space. The plate typically includes a plurality of holes through which fixation elements such as bone screws are inserted to engage underlying bone. Some plating systems include constrained or locking screws, which lock within corresponding plate holes in a fixed orientation. Other plating systems include semi-constrained or non-locking screws, which may move or rotate within plate holes.

SUMMARY OF THE INVENTION

The present invention is directed to a bone fixation element, comprising a shaft extending longitudinally from a proximal end to a distal end and a head connected to the proximal end of the shaft, the head including a radially outer abutting structure deformable to lockingly engage an inner wall of an opening through a bone plate, deformation of the abutting structure permitting the head to lock the bone fixation element within the opening at any user-selected angle with respect to a central axis of the opening within a permitted range of angulation.

BRIEF DESCRIPTION OF THE DRAWINGS

FIG. 8 shows an enlarged cross-sectional perspective view of the device of FIG. 6, inserted into the bone plate using the driving tool;

FIG. 14 shows a perspective view of a device according to a third exemplary embodiment of the present invention, inserted into a bone plate;

FIG. 15 shows a cross-sectional side view of the device of FIG. 14;

FIG. 16 shows a perspective view of a screw or pin according to the device of FIG. 14;

FIG. 20 shows a perspective view of a sleeve according to the device of FIG. 16;

FIG. 21 shows a top view of the sleeve of FIG. 20;

FIG. 22 shows a side view of the sleeve of FIG. 20;

DETAILED DESCRIPTION

Figure 1:
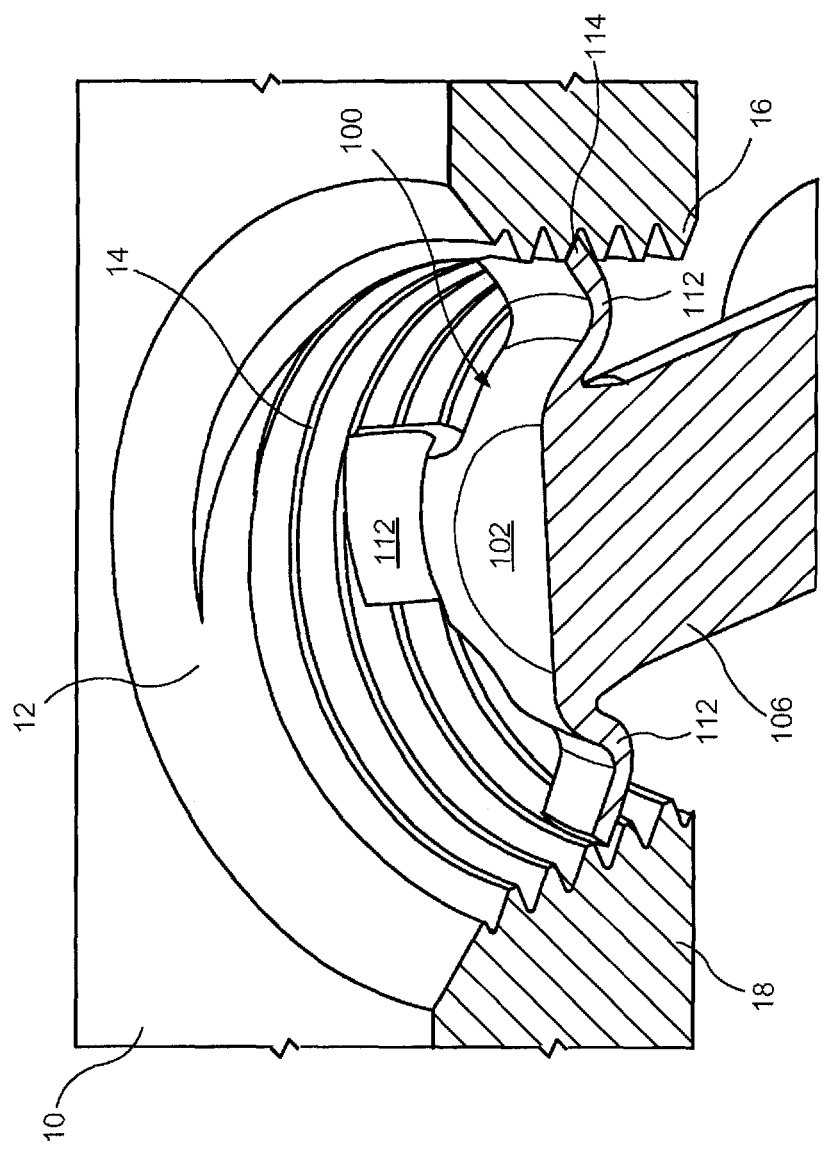
FIG. 1 shows a perspective view of a device according to a first exemplary embodiment of the present invention, inserted into a bone plate.

The present invention may be further understood with reference to the following description and the appended drawings, wherein like elements are referred to with the same reference numerals. The present invention relates to devices for treating fractures and, in particular, relates to devices for fixing implants, such as bone plates, to bone. Exemplary embodiments of the present invention provide a screw or pin that can engage a suitably configured opening of an implant at any of a variety of selectable angles. It should be noted, however, that although the exemplary embodiments describe and show the device as a screw or a pin, the device may be any element capable of fixing the implant to the bone and which is adapted for insertion through an implant at any of a variety of user-selected angles relative thereto. It should also be noted that the terms proximal and distal used herein, are used to describe a direction toward (proximal) and away from (distal) a surgeon or other user of the device.

Figure 2:
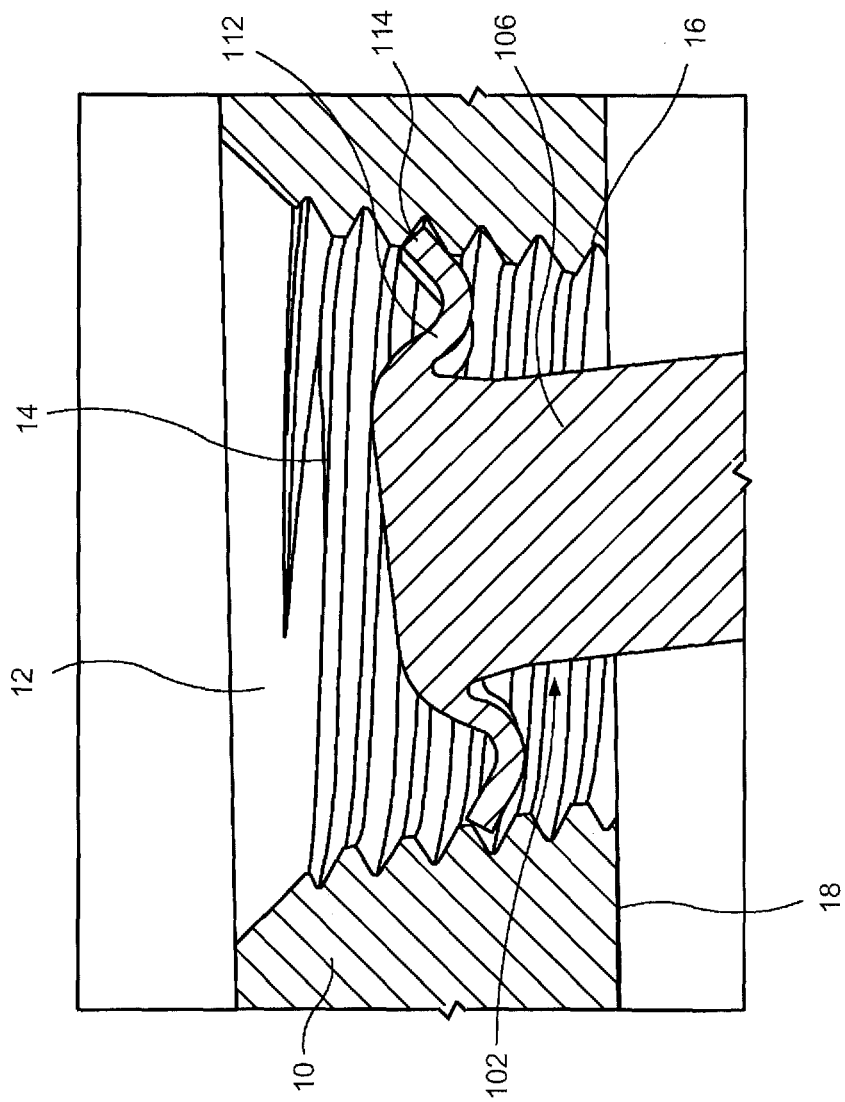
FIG. 2 shows a side view of the device of FIG. 1, inserted into the bone plate.

As shown in FIGS. 1-5, a device 100 according to a first exemplary embodiment of the present invention comprises a head 102 and a shaft 104 connected to one another via a neck portion 106. As shown in FIGS. 1-2, the device 100 may be a screw, pin or other similar device configured to fix a bone plate 10 to a bone. The device 100 may be inserted into an opening 12 of the bone plate 10 such that the head 102 deforms to engages the opening 12, thereby fixing the device 100 to the bone plate 10. The device 100 may be inserted into the opening 12 at an angle selected by a user, i.e., either co-axially with the opening 12 along a central axis thereof or angled relative to the central axis of the opening 12 as selected by a user at the time of the insertion of the device 100 into the opening 12. The opening 12 may be a standard bone plate opening including a threading 14 along at least a portion of the opening 12 as would be understood by those skilled in the art.

Figure 3:
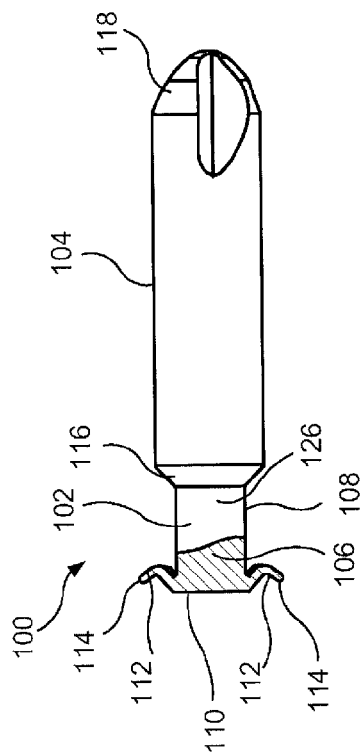
FIG. 3 shows a side view of the device of FIG. 1.
Figure 5:
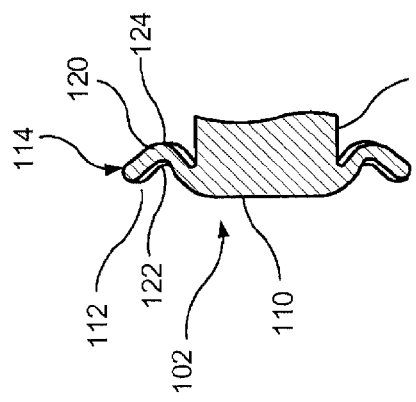
FIG. 5 shows an enlarged cross-sectional side view of a head of the device of FIG. 1.
Figure 4:
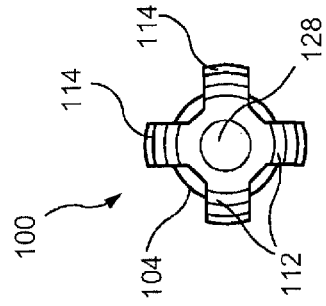
FIG. 4 shows a top view of the device of FIG. 1.

As shown in FIGS. 3-5, the head 102 includes a neck portion 106 and a plurality of bowed elements 112 extending radially outward from a peripheral surface 108 of the neck portion 106 at a proximal end 110 thereof. Each of the bowed elements 112 includes a curved midsection 120 such that a proximal surface 122 of the bowed element 112 is substantially concave while a distal surface 124 thereof is substantially convex. The bowed elements 112 may be thin with a thickness of outer edges 114 thereof substantially corresponding to a pitch of the threading 14—i.e., a thickness of an outer edge 114 is equal to or slightly less than a distance between adjacent turns of the threading 14 in the opening 12 into which it is to be inserted. This allows the outer edges 114 of bowed elements 112 to become lodged between longitudinally adjacent portions of the threading 14 with the bowed elements 112 flexing to accommodate any difference in distance across the opening resulting from the angle selected by the user. That is, the diameter of the head 102 is preferably greater than an inner diameter of the opening 12 so that the bowed elements 112 may engage the threading 14 thereof even when rotated relative to the central axis of the opening 12. For example, a diameter of the opening 12 may be from 0.3 to 0.6 times a diameter of the head 102. The head 102 may include from between 3 to 8 bowed elements 112. In a preferred embodiment, as shown, the head 102 includes four bowed elements 112 spaced substantially equidistantly from one another about the neck portion 106. It will be understood by those of skill in the art, however, that the head 102 may include any number of bowed elements 112 arranged in a variety of patterns about the neck portion 106. The head 102 may be formed of a material that is substantially rigid to lock the head 102 at a desired position within the opening 12, but which is sufficiently flexible to permit the slight deformation of the bowed elements 112 required to engage the threading 14 throughout a desired range of angulation of the device 100 within the opening 12. The head 102 may be formed of a material such as, for example, titanium, TAN, stainless steel, cobalt chrome, PEEK or a polymer.

As described above, a width of the head 102 at the proximal end 110, where the bowed elements 112 are arranged, may be slightly larger than a diameter of the opening 12 such that outer edges 114 of the plurality of bowed elements 112 can engage the threading 14 of the opening 12 regardless of whether the device 100 is inserted co-axially with the opening 12 or at an angle relative to the central axis of the opening 12. Thus, for the opening 12 to accommodate the bowed elements 112, the bowed elements 112 may deform by flexing radially inward, toward the neck portion 106 of the head 102. The outer edge 114 moves toward the neck portion 106 such that a curvature of the curved midsection 120 increases, reducing the diameter of the head 102 at the proximal end 110 to adapt to the size of the opening 12 and the angle of insertion. It will therefore be understood by those of skill in the art that the plurality of bowed elements 112 are preferably designed to engage the opening 12 at any angle within a desired range of angulation of the device 100 relative to the central axis of the opening 12. The flexibility of the plurality of bowed elements 112 may be determined by a number of factors including, but not limited to, the material of the bowed elements 112, a thickness of the bowed elements 112 and a number of bowed elements 112. Thus, it will be understood by those of skill in the art that the flexibility of the bowed elements 112 may be controlled to flex at a desired level.

The shaft 104 extends longitudinally from a proximal end 116 to a distal end 118, with the proximal end 116 connected to a distal end 126 of the neck portion 106 of the head 102. When the device 100 is a bone screw, the shaft 104 may include a threading along at least a portion of a length of the shaft 104 for engaging the bone. The neck portion 106 of the head 102 may be made smaller than a diameter of the shaft 104 to permit enhanced angulation of the device 100 relative to the opening 12 (i.e., by reducing interference between the neck portion 106 and the edge 16 of the opening 12). For example, even when the device 100 is inserted into the opening 12 at an angle relative to the central axis of the opening 12, the reduced diameter of the neck portion 106 provides space to accommodate the edge 16 of the opening 12 at a distal surface 18 of the bone plate 10. It will be understood by those of skill in the art that since the head 102 is flatter than a conventional screw or pin head, the bone plate 10 may be made thinner than standard bone plates which are generally made thick enough to fully accommodate the heads of the screws and/or pins inserted therethrough.

The device 100 may be driven into the opening 12 via a driving tool that engages the head 102 between each of the bowed elements 112 to provide a torque, which rotates the device 100 about a longitudinal axis thereof to rotate the device 100 relative to the opening 12 such that the bowed elements 112 may engage the threading 14. In an alternative embodiment, the device 100 may be driven via a driving element 128 on the proximal surface 108 of the head 102. The driving element may be any recess (e.g., hex recess) or protrusion that is engagable by a mating portion of the driving tool.

An exemplary method for applying the device 100 comprises positioning the bone plate 10 at a desired position on a bone to be treated. Once the bone plate 10 has been positioned as desired, the user inserts the device 100 into one of the openings 12 of the bone plate 10 at an angle selected by the user based, for example, on the characteristics of the bone and the geometry of the plate. The axis along which the device 100 is inserted may be co-axial with the opening 12 or at an angle relative to the central axis of the opening 12 as determined by the user at the time of application of the bone plate 10. In a preferred embodiment, the device 100 may be inserted through the opening 12 at an angle ranging from between 0° and 15° relative to the central axis. For example, the user may pre-drill a hole along a desired axis into which the device 100 is to be inserted through the opening 12. The distal end 118 of the shaft 104 is passed through the opening 12 and the device 100 is driven further distally into the opening 12 (e.g., using any suitable driving tool which engages the head 102). As the device 100 is driven distally through the opening 12, the bowed elements 112 of the head come into contact with the threading 14 of the opening 12 and deform accordingly to engage the threading 14 at various points around the circumference of the opening 12 (and at various levels relative to the central axis thereof depending on the angle of insertion). As described above, the bowed elements 112 flex radially inward toward the neck portion 106 such that the outer edge 114 moves closer to the neck portion 106 and the curvature of the curved midsection 120 of the bowed elements 112 increases. After the bowed elements 112 have flexed in this manner to enter the desired space between adjacent turns of the threading 14, the natural bias of the elements 112 urges them radially outward locking them in place against the threading 14.

Figure 6:
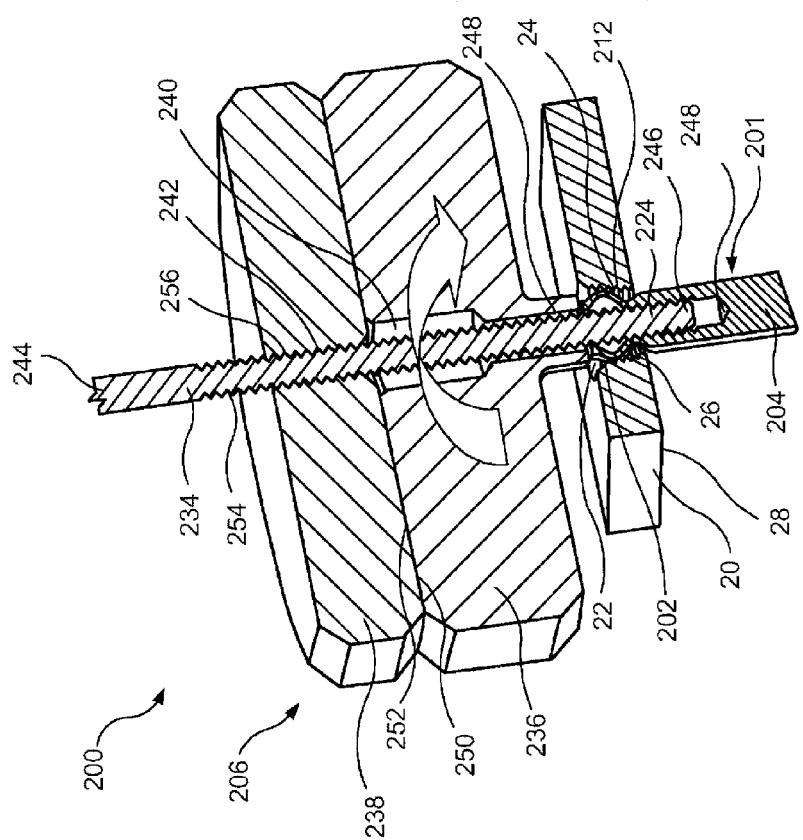
FIG. 6 shows a cross-sectional perspective view of a device according to a second exemplary embodiment of the present invention, inserted into a bone plate using a driving tool.
Figure 7:
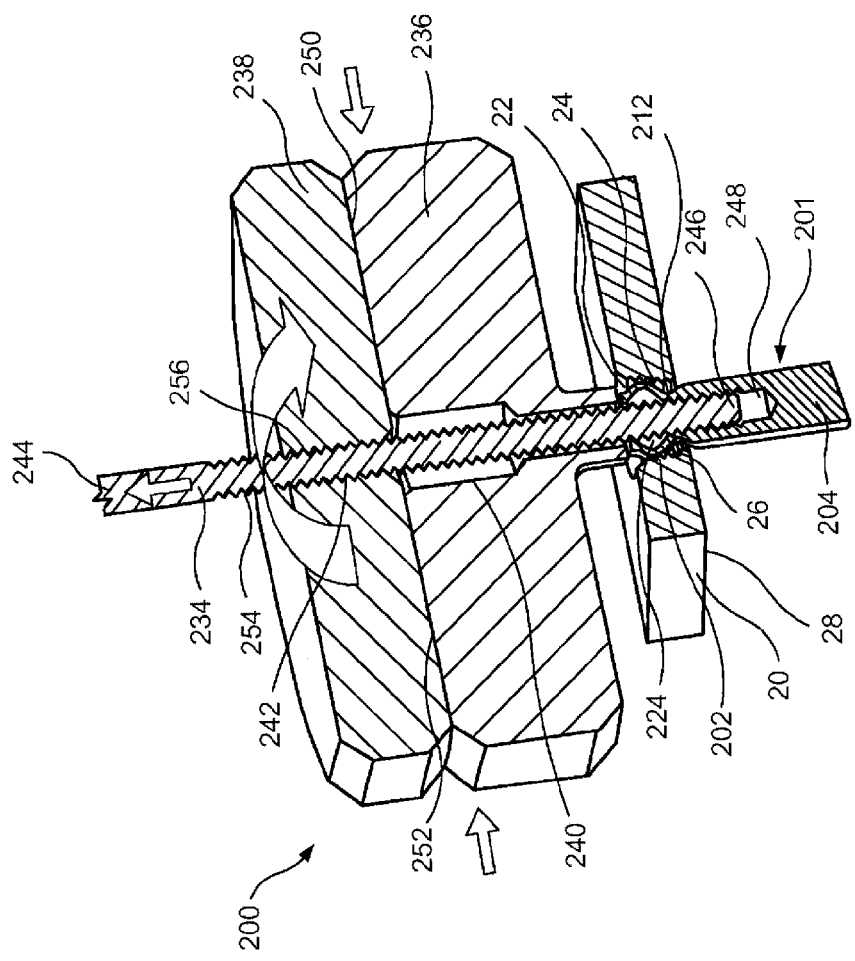
FIG. 7 shows another cross-sectional perspective view of the device of FIG. 6, inserted into the bone plate using the driving tool.
Figure 10:
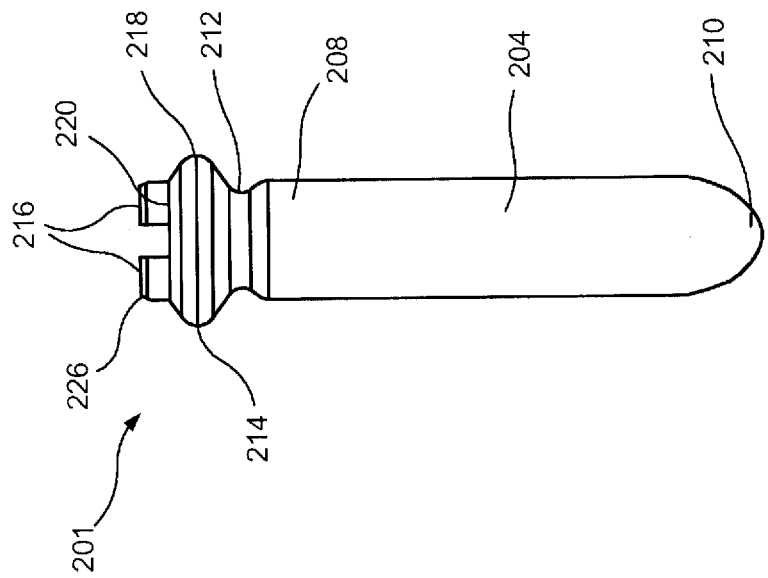
FIG. 10 shows a side view of the device of FIG. 6.
Figure 9:
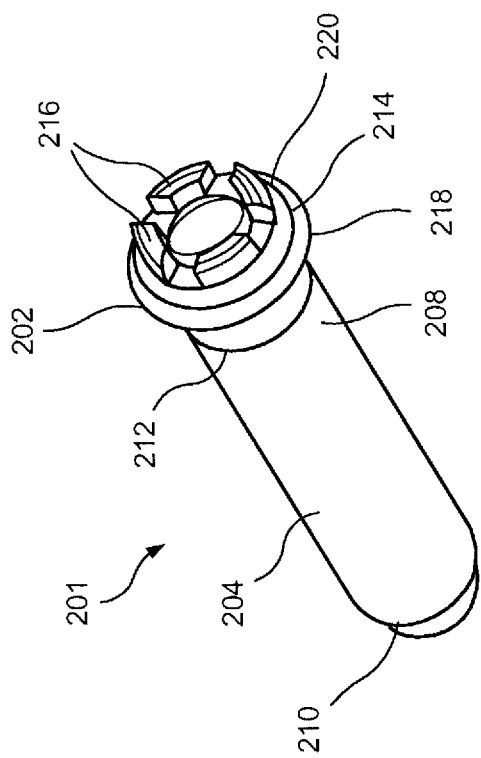
FIG. 9 shows a perspective view of the device of FIG. 6.

As shown in FIGS. 6-12, a system 200 according to a second exemplary embodiment comprises a bone fixation element 201 (e.g., a bone screw or pin) insertable into an opening 22 of an implant 20 via a driving tool 206 at an angle relative to a central axis of the opening 22 that may be selected by a user. The bone fixation element 201 may be inserted into the opening 22 either along the central axis or offset from the central axis of the opening 22 at a user selected angle. As shown in FIGS. 6-8, the bone fixation element 201 may be inserted into the opening 22 using the driving tool 206, which both drives the bone fixation element 201 into the opening 22 and deforms a head portion 202 of the bone fixation element 201 into locking engagement with the opening 22 as will be described in more detail below. The opening 22 of the implant 20 may be, for example, any standard bone plate opening including threading configured to engage, for example, corresponding threading on a head of a standard locking screw or pin to be inserted thereinto. It will be understood by those of skill in the art, however, that the opening 22 may also be non-threaded, cylindrical, ball-shaped, conical, etc. It will also be understood by those of skill in the art that the implant 20 should have a depth sufficient to fully accommodate a length of the head portion 202 of the bone fixation element 201 (i.e., so that when the bone fixation element is fully seated in the opening 22, the head portion 202 does not protrude therefrom).

The bone fixation element 201, as shown in FIGS. 9-12, includes the head 202 connected to a proximal end 208 of a shaft 204. The head 202 includes, for example, an engaging portion 214 and a driving element 216 extending proximally therefrom. The engaging portion 214 may be substantially rounded and has a diameter selected so that an outer surface 218 thereof engages the sides of the opening 22 when the head 202 is deformed as described below. The driving element 216 extends from a proximal end 220 of the engaging portion 214 and may be used to engage a driving tool 206 to drive the bone fixation element 201 through the opening 22. The driving element 216 may include a single protrusion or a plurality of protrusions coupleable with a portion of the driving tool 206. In the example shown, the driving element 216 includes a plurality of protrusions spaced substantially equidistantly from one another about a longitudinal axis of the bone fixation element 201 so that, when connected, the plurality of protrusions forms a substantially ring-like driving element 216. In use, the driving element 216 is coupled to the driving tool 206 so that the driving tool may provide a torque on the bone fixation element 201, thereby rotating the bone fixation element 201 about the longitudinal axis to drive the bone fixation element 201 through the opening 22.

Figure 13:
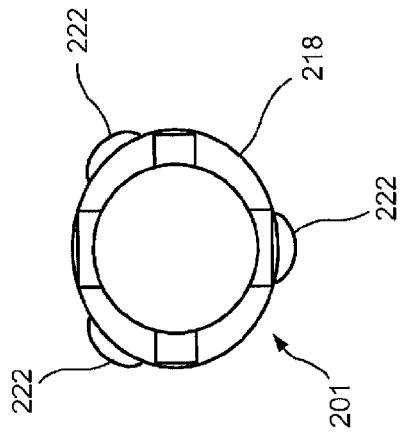
FIG. 13 shows a top view of a device according to a further embodiment of the present invention.
Figure 12:
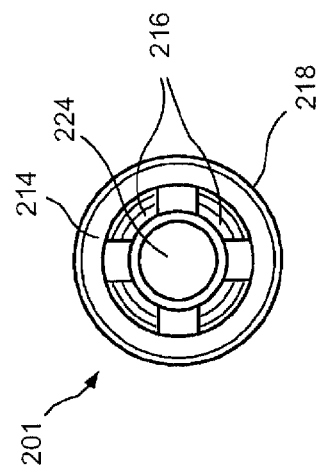
FIG. 12 shows a top view of the device of FIG. 6.
Figure 11:
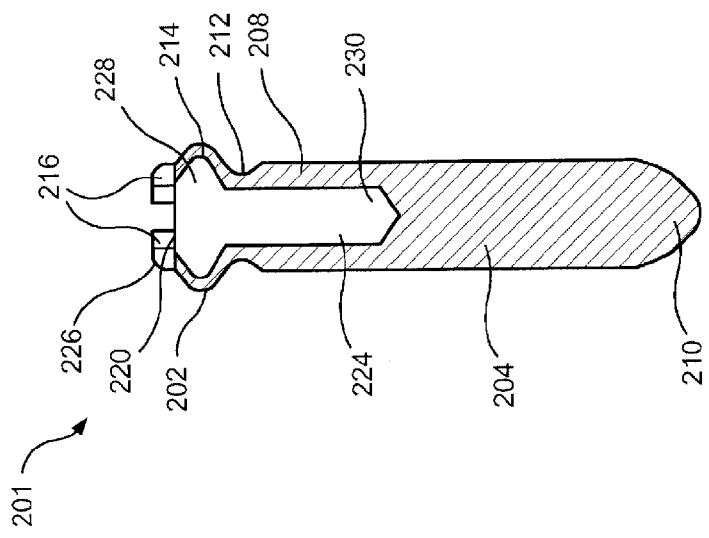
FIG. 11 shows a cross-sectional side view of the device of FIG. 6.

In a further embodiment, as shown in FIG. 13, the engaging portion 214 of the head 202 also includes a plurality of engaging elements 222 protruding radially outward (i.e., away from the axis of the shaft 204) from the outer surface 218 of the first protrusion 214 to provide an initial grip between the head 202 and the opening 22 by engaging the threads 24. The plurality of engaging elements 222 may be formed about a perimeter of the engaging portion 214 at which a width of the engaging portion 214 is largest. A device according to an exemplary embodiment of the invention may include from three to six engaging elements 222 distributed in any desired pattern about a circumference of the surface 218. However, it will be understood by those of skill in the art that any number of engaging elements 222 may be included to achieve the desired initial gripping.

The shaft 204 extends longitudinally from the proximal end 208 to a distal end 210 and, when the bone fixation element 201 is a screw, may include a thread along at least a portion of a length thereof. The proximal end 208 of the shaft 204 is connected to the engaging portion 214 of the head 202 via a neck portion 212 which has a diameter smaller than a diameter of the shaft 204 and/or the engaging portion 214 of the head 202 to provide space facilitating angulation of the bone fixation element 201 in the same manner described above. For example, the neck portion 212 may accommodate an edge 26 of the opening 22 at a distal surface 28 of the implant 20, the distal surface 28 facing the bone so that contact between these elements does not hinder angulation of the bone fixation element 201.

The bone fixation element 201 further includes a channel 224 extending from an opening in a proximal end 226, through the head 202 and through at least a portion of a length of the shaft 204. The channel 224 is sized and shaped to be engaged by a rod 234 of the driving tool 206 for deforming the head 202 of the bone fixation element 201. The channel 224 may also correspond to a shape of the head 202 and the shaft 204. For example, a first portion 228 of the channel 224, located within the engaging portion 214 of the head 202, may be correspondingly rounded such that a thickness of the engaging portion 214 between the outer surface 218 of the engaging portion 214 of the head 202 and an inner surface 232 of the first portion 228 of the channel 224 is substantially consistent along a length of the head 202. A second portion 230 of the channel 224 extending through a portion of a length of the shaft 204 may be substantially cylindrical, corresponding to the longitudinal shape of the shaft 204.

The driving tool 206, as shown in FIGS. 6-8, comprises a first nut 236, a second nut 238 and the rod 234. Each of the first and second nuts 236, 238 includes a lumen 240, 242, respectively, for accommodating the rod 234. The rod 234 extends longitudinally from a proximal end 244 to a distal end 246. The distal portion 246 of the rod threadedly engages a distal portion 248 of the channel 224 while a remaining length of the rod 234 extends through the lumens 240, 242. The first nut 236 acts as a wrench nut and includes a driving element 248 for mating with the second portion 216 of the head 202, while abutting the engaging portion 214. A diameter of the lumen 240 of the first nut 236 is slightly larger than a diameter of the rod 234 such that the rod 234 is slidable therethrough. The second nut 238 is positioned proximally of the first nut 236 with a distal surface 250 of the first nut 238 contacting a proximal surface 252 of the first nut 236. The lumen 242 of the second nut 238 includes a thread 256 corresponding to a thread 254 of the rod 234. Therefore, the thread 256 engages the thread 254 such that the rod 234 and the second nut 238 move longitudinally relative to one another when they are rotated relative to one another. Specifically, rotation of the rod 234 and the second nut 238 relative to one another about the longitudinal axis causes the rod 234 to move longitudinally along the longitudinal axis while rotating about the longitudinal axis.

An exemplary method of use of the system 200 comprises positioning the bone plate 20 at a desired location on a target bone. Once the bone plate 20 is positioned, the user inserts a bone fixation element 201 the opening 22 of the bone plate 20 at an angle selected by the user (co-axially or offset relative to the central axis of the opening 22) in the same manner described above. For example, the bone fixation element 201 may be inserted through the opening 22 at an angle ranging from between 0° and 15°. The distal end 210 of the shaft 204 is inserted into the opening 22 and the bone fixation element 201 is driven further distally therethrough using the driving tool 206. Specifically, the first nut 236, which mates with the bone fixation element 201 via the driving element 248, is rotated about the longitudinal axis, thereby rotating the bone fixation element 201 about the axis of insertion and driving the bone fixation element 201 through the opening 22. The bone fixation element 201 may be driven distally therethrough until the head 202 is substantially within the opening 22. Once the bone fixation element 201 is in an appropriate position within the opening 22, the second nut 238 may be rotated relative to the rod 234 which threadedly engages the channel 224. Rotation of the second nut 238 moves the rod 234 proximally along the longitudinal axis relative to the second nut 238. Since the second nut 238 is in contact with the first nut 236, which is located distally thereof, the second nut 238 exerts a distally directed force on the first nut 236, which in turn exerts a distal force against the bone fixation element 201 via the driving element 248, which abuts the engaging portion 214 of the head 202. Simultaneously, as the rod 234 moves proximally relative to the second nut 238, the bone fixation element 201, which is attached to the distal portion 246 of the rod 234, is drawn proximally forcing the engaging portion 214 of the head 202 against the driving element 248. As the driving element 248 is exerting a distally directed force against the head 202 at the same time, the'head 202 is squeezed against the driving element 248 causing the head 202 to deform and expand radially outward away from the axis of the shaft 204. That is, as the length of the head 202 along the axis of the shaft 204 shortens, the radius of the head 202 expands forcing the outer surface 218 thereof into locking engagement with the inner surface of the opening 22 (e.g., the threading 24) and fixing the bone fixation element 201 at a desired position and angle within the opening 22. Once the desired level of deformation has occurred, the driving tool 206 may be removed from the bone fixation element 201. The rod 234 is then unscrewed from the second nut 238 and the channel 224 and withdrawn from the body. The driving element 248 may then be de-coupled from the protrusions 216 and the first and second nuts 236, 238, respectively, are withdrawn from the body.

As shown in FIGS. 14-22, a device 300 according to a third exemplary embodiment of the present invention includes a sleeve 306 and a bone fixation element 301 which may, for example, be a bone pin or screw. As shown in FIG. 14, the device 300 may be inserted into an opening 32 of a bone plate 30 either co-axially with the opening 32 along a central axis of the opening 32 or at an angle relative to the central axis as desired by the user. The opening 32 may be any standard bone plate opening and may include a threading 34 along at least a portion of the opening 32. As shown in FIG. 15, the sleeve 306 of the device 300 may be molded on a head 302 of the bone fixation element 301 such that the sleeve 306 is deformable (i.e., expandable) to engage with the inner surface of the opening 32 (e.g., the threading 34). The bone fixation element 301 further includes a shaft 304 extending longitudinally between a proximal end 308 connected to the head 302 and a distal end 310. As would be understood by those skilled in the art, if the bone fixation element 301 is a screw, the shaft 304 will include threading along at least a portion of a length thereof for engaging with the bone.

Figure 19:
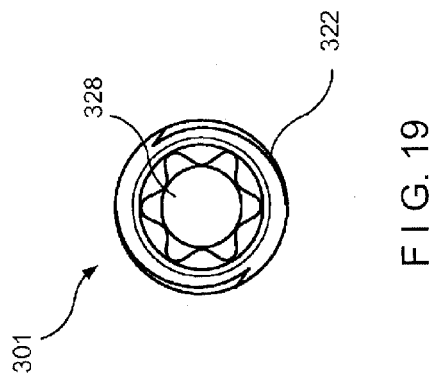
FIG. 19 shows a top view of the screw or pin of FIG. 16.
Figure 18:
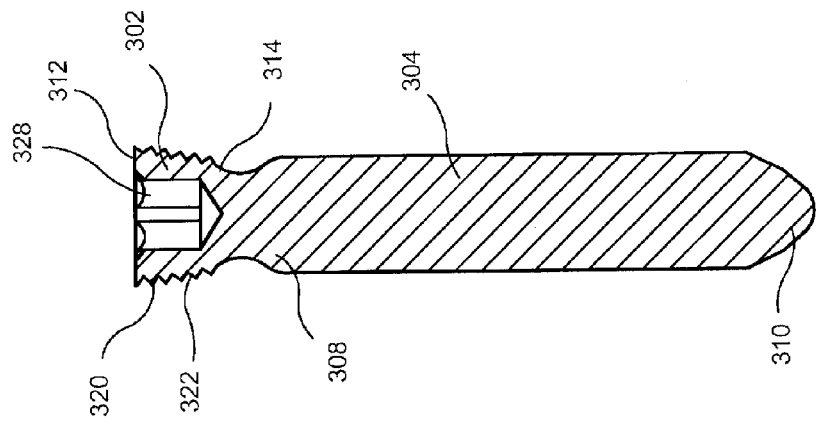
FIG. 18 shows a cross-sectional side view of the screw or pin of FIG. 16.
Figure 17:
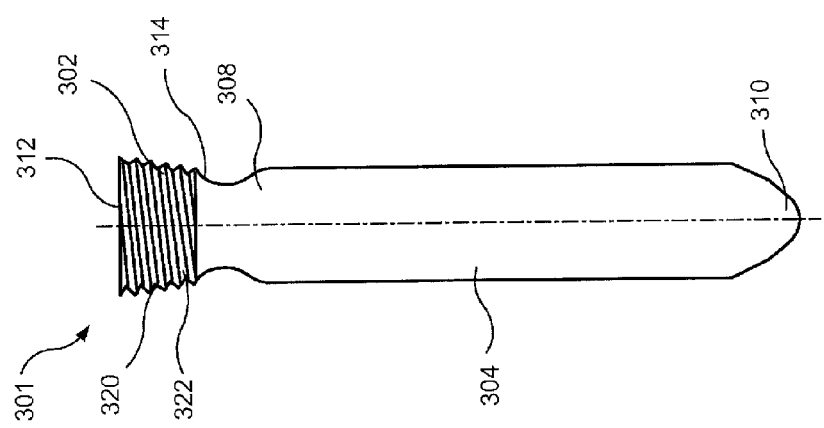
FIG. 17 shows a side view of the screw or pin of FIG. 16.

As shown in FIGS. 16-19, the head 302 of the bone fixation element 301 may be substantially conically shaped with a diameter of a proximal end 312 of the head 302 being larger than a diameter of a distal end 314 of the head 302. A taper angle of the head 302 may range from approximately 10° to 30° relative to a longitudinal axis of the bone fixation element 301. The head 302 may further include a threading 318 about an outer surface 316 of the head 302, along at least a portion of a length of the head 302. The threading 322 may be a continuous helical thread formed at a consistent pitch about the outer surface 316 or a series of separate circular threads. The head 302, as shown in FIGS. 18-19, may also include a driving element 328 at a the proximal end 312 such as a hex recess. It will be understood by those of skill in the art, however, that the driving element 328 may be any recess, protrusion or other structure engagable by a driving tool to drive the device 300 distally through the opening 32.

As shown in FIG. 15, the sleeve 306 may be molded on a portion of the outer surface 316 of the head 302. The sleeve 306 is preferably formed of a soft material such as polyetheretherketone (PEEK), such that the sleeve 306 may be expanded to be fixed within the opening 32 and anchor the bone fixation element 301 relative to the bone plate 30. The sleeve 306 may also be formed of other materials such as pure titanium and any of a variety of plastics. As shown in FIGS. 20-22, the sleeve 306 includes at least one protrusion 320 about at least a portion of a circumference of an outer surface 322 of the sleeve 306. The at least one protrusion 320 may be formed on the outer surface 322 as a continuous protrusion about the circumference. Alternatively, the at least one protrusion 320 may be formed as a series of protrusions extending along a path about the outer surface 322 or in any other pattern suitable to lockingly engage the opening 32. The protrusion 320 is formed on the outer surface 322 such that when the device 300 is inserted into the opening 32, the protrusion 320 engages with the threading 34 of the opening 32.

The outer surface 322 may include both a plurality of rounded portions 330 and a plurality of planar portions 332 such that adjacent ones of the rounded portions 330 are separated by one of the planar portions 332. The planar portions 332 may be substantially parallel to a central axis of the sleeve 306, reducing a width of a proximal end 334 of the sleeve 306 such that the sleeve 306 may be inserted into the opening 34 at a variable angle. The planar portions 332 may extend along a portion of a length of the sleeve 306. It will be understood by those of skilled in the art that the at least one protrusion 320 may be formed along the rounded portions 330.

Since the sleeve 306 is molded onto the head 302, an inner surface 324 of the sleeve 306, which contacts the outer surface 316 of the head 302, adopts a shape of the outer surface 316, including the threading 318. Thus, as the sleeve 306 is molded over the head 302, the inner surface 324 of the sleeve 306 is formed to include a threading 326 corresponding to the threading 318 of the head 302. When the bone fixation element 301 is rotated about the longitudinal axis, relative to the sleeve 306, the bone fixation element 301 moves longitudinally relative to the sleeve 306 as the threading 318 slides through the corresponding threading 326 of the sleeve 306. Since the head 302 of the screw or pin 302 is substantially conical, as the head 302 moves distally through the sleeve 306, progressively larger diameter portions of the head 302 move into and deform the sleeve 306 expanding the sleeve 306 and forcing the protrusion(s) 320 into locking engagement with the opening 32.

According to an exemplary method of use of the device 300, the bone plate 30 is placed against a target portion of bone to be treated and, once the bone plate 30 has been positioned as desired, the distal end 310 of the shaft 304 of the device 300 is inserted into one of the openings 32. The device 300 is passed through the opening 32 into, for example, a pre-drilled hole extending either coaxially with the opening 32 or at an angle offset relative to the central axis of the opening 32 by a predetermined amount and driven through the opening 32 into the bone in a conventional manner—e.g., using a driving tool. The driving tool may engage the driving element 328 to rotate the device 300 about a longitudinal axis thereof until the head 302 and the sleeve 306 are substantially within the opening 32 with the protrusion 320 engaging the threading 34. Once the protrusion 320 has engaged the threading 34, continuous rotation via the driving element 328 will cause a bond between the head 302 and the sleeve 306 to break such that the bone fixation element 301 is driven distally relative to the sleeve 306. The bone fixation element 301 moves longitudinally relative to the sleeve 306 such that the threading 318 of the head 302 slides through the threading 326 of the sleeve 306. As the bone fixation element 301 moves distally through the sleeve 306, the progressively larger diameter of proximal portions of the head 302 cause the sleeve 306 to deform by expanding to accommodate the progressively larger proximal portions of the head 302. Thus, the sleeve 306 expands, strengthening the engagement between the device 300 and the opening 32, thereby fixing the device 300 relative to the bone plate 30.

Figure 23:
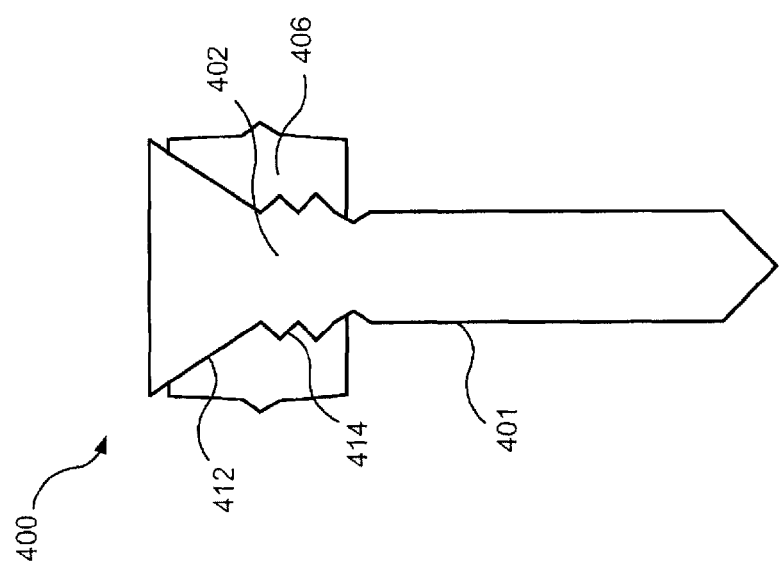
FIG. 23 shows a cross-sectional side view of a device according to a fourth exemplary embodiment of the present invention.

As shown in FIG. 23, a device 400 according to a fourth exemplary embodiment of the present invention may be substantially similar to the device 300, as described above. The device 400 comprises a bone fixation element 401 and a sleeve 406 molded onto a head 402 of the bone fixation element 401. The bone fixation element 401 is substantially similar to the bone fixation element 301 except that the head 402 includes a substantially conically shaped proximal portion 412 and a threaded distal portion 414. Thus, the threaded distal portion 414 allows the bone fixation element 401 to be driven distally relative to the sleeve 406 while the proximal portion 412 causes the sleeve 406 to deform by expanding.

Figure 24:
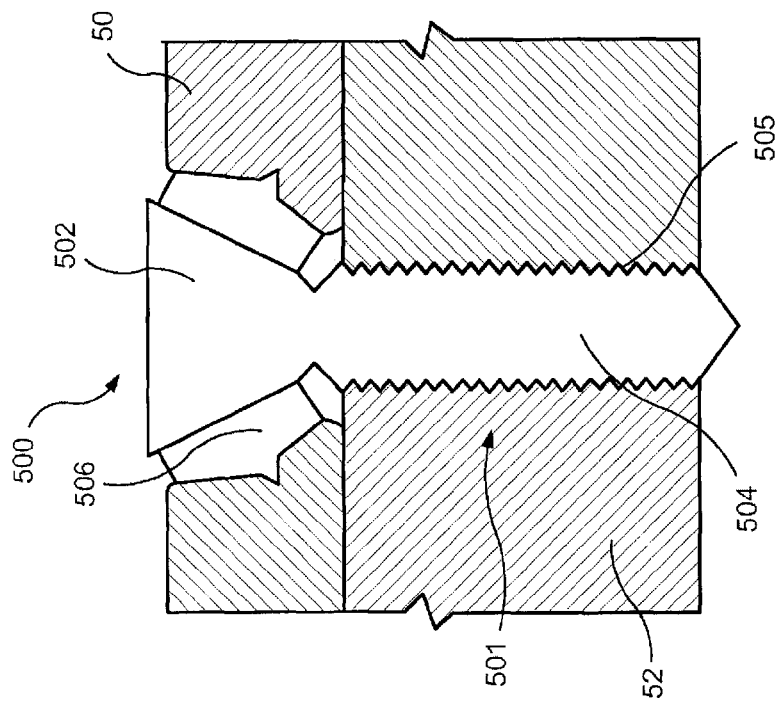
FIG. 24 shows a cross-sectional side view of a device according to a fifth exemplary embodiment of the present invention.

As shown in FIG. 24, a device 500 according to a fifth exemplary embodiment of the present invention may be substantially similar to the device 300, as described above. The device 500 comprises a bone fixation element 501 and a sleeve 506 molded to a head 502 of the bone fixation element. The bone fixation element 501 is a screw including a substantially conical head 502 and a shaft 504 that includes a threading 505 along at least a portion of a length thereof. The threading 505 of the shaft 504 allows the bone fixation element 501 to be driven distally relative to the sleeve 506 and a bone plate 50, through which the device 500 is inserted, such that the bone fixation element 501 moves toward a bone 52 to compress the bone plate 50 to the bone 52. As the bone fixation element 501 moves distally relative to the sleeve 506, the conical head 502 causes the sleeve 506 to deform by expanding.

Figure 26:
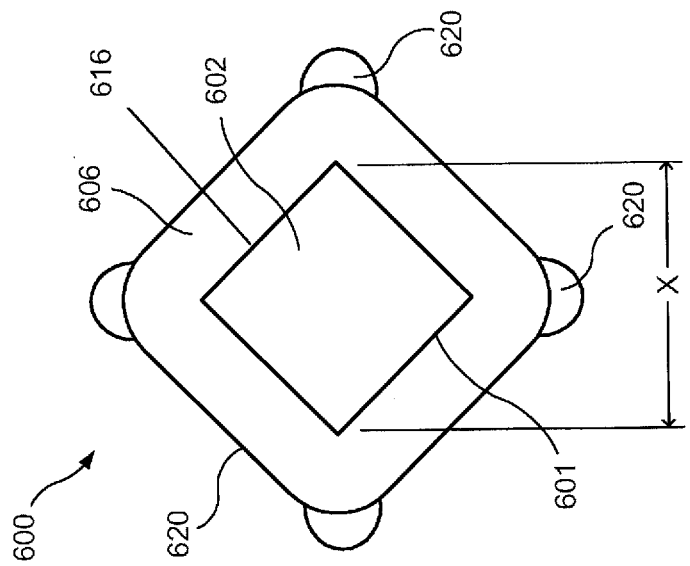
FIG. 26 shows a top view of a device according to the device of FIG. 25, in a second configuration.
Figure 25:
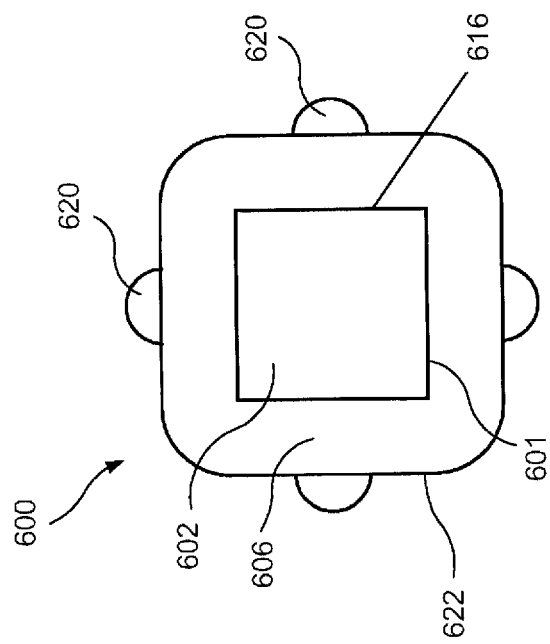
FIG. 25 shows a top view of a device according to a sixth exemplary embodiment of the present invention, in a first configuration.

As shown in FIGS. 25-26, a device 600 according to a sixth exemplary embodiment of the present invention may be substantially similar to the device 300, as described above. The device 600 comprises a bone fixation element 601 and a sleeve 606 molded to a head 602 of the bone fixation element 601. The bone fixation element 601 may be substantially similar to the bone fixation element 301, except that the head 602 is substantially non-circular. An outer surface 616 of the head 602 may include a threading or protrusion for mating with the sleeve 606. In a preferred embodiment, a lateral cross-section of the head 602 may be substantially square such that rotating the bone fixation element 601 45° relative to the sleeve 606 deforms the sleeve 606 expanding it radially outward. For example, in a first configuration, as shown in FIG. 25, a diagonal X of the head 602 may not correspond to a protrusion 620 on an outer surface 622 of the sleeve 606. The bone fixation element 601 may be rotated to a second configuration, as shown in FIG. 26, in which the diagonal X is substantially aligned with the protrusion 620, deforming the sleeve 606 such that a portion of the sleeve 606 including the protrusion 620 expands. It will be understood by those of skill in the art that although the head 602 is shown to be substantially square, the head 602 may be any non-circular shape so long as rotation of the head 602 relative to the sleeve 606 deforms the sleeve 606 radially outward in a manner similar to that described above. It will also be understood by those of skill in the art that the shape of the head 602 will determine a degree of rotation required to deform the sleeve 606 to the desired degree.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A bone fixation element, comprising:
a shaft extending longitudinally from a proximal end to a distal end; and
a head connected to the proximal end of the shaft, the head including a radially outer abutting structure deformable to lockingly engage an inner wall of an opening through a bone plate, deformation of the abutting structure permitting the head to lock the bone fixation element within the opening at any user-selected angle with respect to a central axis of the opening within a permitted range of angulation, wherein the abutting structure is shaped so that, when compressed along a longitudinal axis of the shaft, the abutting structure expands radially outward from the longitudinal axis of the shaft to engage an inner wall of an opening within which it is received.

2. The bone fixation element of claim 1, wherein the head is compressible along an axis of the shaft so that, when axially compressed, the head expands radially outward from the axis of the shaft to engage an inner surface of the opening.

3. The bone fixation element of claim 2, further comprising a channel extending from a proximal end of the bone fixation element through the head and a portion of the shaft, a first portion of the channel corresponding to a shape of the head and a second portion of the channel corresponding to a shape of the shaft.

4. The bone fixation element of claim 3, wherein the portion of the channel extending within the shaft is threaded to releasably engage a threaded rod inserted thereinto.

5. The bone fixation element of claim 3, wherein the head including a driving element at a proximal end thereof, the driving element removably coupleable with a driving tool for driving the bone fixation element distally through the opening of a bone plate while the threaded rod draws the shaft of the bone fixation element proximally, axially compressing and radially expanding the head.

6. The bone fixation element of claim 1, further comprising:
a channel extending into the shaft from a proximal end of the head, the channel sized to receive and engage a rod of a drive tool; and
at least one first driving element joined to the head and oriented to engage a at least one second driving element of a drive tool.

* * * * *